United States Patent
Morton

(10) Patent No.: US 9,057,679 B2
(45) Date of Patent: Jun. 16, 2015

(54) COMBINED SCATTER AND TRANSMISSION MULTI-VIEW IMAGING SYSTEM

(71) Applicant: Rapiscan Systems, Inc., Torrance, CA (US)

(72) Inventor: Edward James Morton, Guildford (GB)

(73) Assignee: Rapiscan Systems, Inc., Torrance, CA (US)

( * ) Notice: Subject to any disclaimer, the term of this patent is extended or adjusted under 35 U.S.C. 154(b) by 180 days.

(21) Appl. No.: 13/756,211

(22) Filed: Jan. 31, 2013

(65) Prior Publication Data

US 2014/0044233 A1 Feb. 13, 2014

Related U.S. Application Data

(60) Provisional application No. 61/594,625, filed on Feb. 3, 2012.

(51) Int. Cl.
| | |
|---|---|
| *G01N 23/087* | (2006.01) |
| *G01N 23/203* | (2006.01) |
| *H05G 1/70* | (2006.01) |
| *G01N 23/04* | (2006.01) |
| *G01V 5/00* | (2006.01) |

(52) U.S. Cl.
CPC .............. *G01N 23/04* (2013.01); *G01V 5/0066* (2013.01); *H05G 1/70* (2013.01); *G01V 5/0033* (2013.01); *G01N 23/203* (2013.01); *G01V 5/0008* (2013.01); *G01V 5/0025* (2013.01)

(58) Field of Classification Search
CPC . G01V 5/0008; G01V 5/0016; G01V 5/0025; G01V 5/0033; G01V 5/0066; G01N 23/203; H05G 1/70

USPC .......... 378/57, 62, 86–92, 95, 98.8, 119, 121, 378/146, 147, 149–151, 204, 210; 250/370.01, 370.08, 370.09, 370.1, 250/370.11, 370.12, 370.13, 370.14, 374, 250/382, 487.1

See application file for complete search history.

(56) References Cited

U.S. PATENT DOCUMENTS

| | | |
|---|---|---|
| 2,831,123 A | 4/1958 | Daly |
| 3,766,387 A | 10/1973 | Heffan |
| 3,784,837 A | 1/1974 | Holmstrom |

(Continued)

FOREIGN PATENT DOCUMENTS

| | | |
|---|---|---|
| EP | 0261984 A2 | 3/1988 |
| EP | 0864884 A2 | 9/1998 |

(Continued)

OTHER PUBLICATIONS

International Search Report and Written Opinion for PCT/US2010/041757, Oct. 12, 2010.

(Continued)

*Primary Examiner* — Anastasia Midkiff
(74) *Attorney, Agent, or Firm* — Novel IP

(57) ABSTRACT

The present specification discloses a multi-view X-ray inspection system having, in one of several embodiments, a three-view configuration with three X-ray sources. Each X-ray source rotates and is configured to emit a rotating X-ray pencil beam and at least two detector arrays, where each detector array has multiple non-pixellated detectors such that at least a portion of the non-pixellated detectors are oriented toward both the two X-ray sources.

7 Claims, 10 Drawing Sheets

(56) References Cited

U.S. PATENT DOCUMENTS

| | | |
|---|---|---|
| RE28,544 E | 9/1975 | Stein |
| 3,961,186 A | 6/1976 | Leunbach |
| 4,047,035 A | 9/1977 | Dennhoven |
| 4,064,440 A | 12/1977 | Roder |
| 4,139,771 A | 2/1979 | Dennhoven |
| 4,210,811 A | 7/1980 | Dennhoven |
| 4,216,499 A | 8/1980 | Dennhoven |
| 4,366,382 A | 12/1982 | Kotowski |
| 4,380,817 A | 4/1983 | Harding |
| 4,430,568 A | 2/1984 | Yoshida |
| 4,525,854 A | 6/1985 | Molbert |
| 4,566,113 A | 1/1986 | Doenges |
| 4,599,740 A | 7/1986 | Cable |
| 4,641,330 A | 2/1987 | Herwig |
| 4,736,401 A | 4/1988 | Donges |
| 4,754,469 A | 6/1988 | Harding |
| 4,788,704 A | 11/1988 | Donges |
| 4,789,930 A | 12/1988 | Sones |
| 4,799,247 A | 1/1989 | Annis |
| 4,809,312 A | 2/1989 | Annis |
| 4,825,454 A | 4/1989 | Annis |
| 4,864,142 A | 9/1989 | Gomberg |
| 4,870,670 A | 9/1989 | Geus |
| 4,884,289 A | 11/1989 | Glockmann |
| 4,956,856 A | 9/1990 | Harding |
| 4,979,202 A | 12/1990 | Siczek |
| 4,991,189 A | 2/1991 | Boomgaarden |
| 5,007,072 A | 4/1991 | Jenkins |
| 5,008,911 A | 4/1991 | Harding |
| 5,022,062 A | 6/1991 | Annis |
| 5,065,418 A | 11/1991 | Bermbach |
| 5,091,924 A | 2/1992 | Bermbach |
| 5,098,640 A | 3/1992 | Gozani |
| 5,179,581 A | 1/1993 | Annis |
| 5,181,234 A | 1/1993 | Smith |
| 5,182,764 A | 1/1993 | Peschmann |
| 5,224,144 A | 6/1993 | Annis |
| 5,237,598 A | 8/1993 | Albert |
| 5,247,561 A | 9/1993 | Kotowski |
| 5,253,283 A | 10/1993 | Annis |
| 5,263,075 A | 11/1993 | McGann |
| 5,265,144 A | 11/1993 | Harding |
| 5,313,511 A | 5/1994 | Annis |
| 5,367,552 A | 11/1994 | Peschmann |
| 5,379,334 A | 1/1995 | Zimmer |
| 5,394,454 A | 2/1995 | Harding |
| 5,420,905 A | 5/1995 | Bertozzi |
| 5,430,787 A | 7/1995 | Norton |
| 5,493,596 A | 2/1996 | Annis |
| 5,524,133 A | 6/1996 | Neale |
| 5,600,303 A | 2/1997 | Husseiny |
| 5,600,700 A | 2/1997 | Krug |
| 5,638,420 A | 6/1997 | Armistead |
| 5,642,393 A | 6/1997 | Krug |
| 5,642,394 A | 6/1997 | Rothschild |
| 5,666,393 A | 9/1997 | Annis |
| 5,687,210 A | 11/1997 | Maitrejean |
| 5,692,028 A | 11/1997 | Geus |
| 5,692,029 A | 11/1997 | Husseiny |
| 5,696,806 A | 12/1997 | Grodzins |
| 5,745,543 A | 4/1998 | De Bokx |
| 5,751,837 A | 5/1998 | Watanabe |
| 5,763,886 A | 6/1998 | Schulte |
| 5,764,683 A | 6/1998 | Swift |
| 5,768,334 A | 6/1998 | Maitrejean |
| 5,787,145 A | 7/1998 | Geus |
| 5,805,660 A | 9/1998 | Perion |
| 5,838,759 A | 11/1998 | Armistead |
| 5,903,623 A | 5/1999 | Swift |
| 5,910,973 A | 6/1999 | Grodzins |
| 5,930,326 A | 7/1999 | Rothschild |
| 5,940,468 A | 8/1999 | Huang |
| 5,974,111 A | 10/1999 | Krug |
| 6,018,562 A | 1/2000 | Willson |
| 6,031,890 A | 2/2000 | Bermbach |
| 6,054,712 A | 4/2000 | Komardin |
| 6,058,158 A | 5/2000 | Eiler |
| 6,067,344 A | 5/2000 | Grodzins |
| 6,081,580 A | 6/2000 | Grodzins |
| 6,094,472 A | 7/2000 | Smith |
| 6,118,850 A | 9/2000 | Mayo |
| 6,128,365 A | 10/2000 | Bechwati |
| 6,151,381 A | 11/2000 | Grodzins |
| 6,188,747 B1 | 2/2001 | Geus |
| 6,192,101 B1 | 2/2001 | Grodzins |
| 6,192,104 B1 | 2/2001 | Adams |
| 6,195,413 B1 | 2/2001 | Geus |
| 6,198,795 B1 | 3/2001 | Naumann |
| 6,212,251 B1 | 4/2001 | Tomura |
| 6,218,943 B1 | 4/2001 | Ellenbogen |
| 6,236,709 B1 | 5/2001 | Perry |
| 6,249,567 B1 | 6/2001 | Rothschild |
| 6,252,929 B1 | 6/2001 | Swift |
| 6,256,369 B1 | 7/2001 | Lai |
| 6,278,115 B1 | 8/2001 | Annis |
| 6,282,260 B1 | 8/2001 | Grodzins |
| 6,292,533 B1 | 9/2001 | Swift |
| 6,301,326 B2 | 10/2001 | Bjorkholm |
| 6,320,933 B1 | 11/2001 | Grodzins |
| 6,356,620 B1 | 3/2002 | Rothschild |
| 6,421,420 B1 | 7/2002 | Grodzins |
| 6,424,695 B1 | 7/2002 | Grodzins |
| 6,434,219 B1 | 8/2002 | Rothschild |
| 6,435,715 B1 | 8/2002 | Betz |
| 6,442,233 B1 | 8/2002 | Grodzins |
| 6,445,765 B1 | 9/2002 | Frank |
| 6,453,003 B1 | 9/2002 | Springer |
| 6,453,007 B2 | 9/2002 | Adams |
| 6,456,684 B1 | 9/2002 | Mun |
| 6,459,761 B1 | 10/2002 | Grodzins |
| 6,459,764 B1 | 10/2002 | Chalmers |
| 6,473,487 B1 | 10/2002 | Le |
| RE37,899 E | 11/2002 | Grodzins |
| 6,483,894 B2 | 11/2002 | Hartick |
| 6,507,025 B1 | 1/2003 | Verbinski |
| 6,532,276 B1 | 3/2003 | Hartick |
| 6,542,574 B2 | 4/2003 | Grodzins |
| 6,542,578 B2 | 4/2003 | Ries |
| 6,542,580 B2 | 4/2003 | Carver |
| 6,543,599 B2 | 4/2003 | Jasinetzky |
| 6,546,072 B1 | 4/2003 | Chalmers |
| 6,552,346 B2 | 4/2003 | Verbinski |
| 6,556,653 B2 | 4/2003 | Hussein |
| 6,563,903 B2 | 5/2003 | Kang |
| 6,567,496 B1 | 5/2003 | Sychev |
| 6,580,778 B2 | 6/2003 | Meder |
| 6,584,170 B2 | 6/2003 | Aust |
| 6,597,760 B2 | 7/2003 | Beneke |
| 6,606,516 B2 | 8/2003 | Levine |
| 6,628,745 B1 | 9/2003 | Annis |
| 6,636,581 B2 | 10/2003 | Sorenson |
| 6,653,588 B1 | 11/2003 | Gillard-Hickman |
| 6,658,087 B2 | 12/2003 | Chalmers |
| 6,663,280 B2 | 12/2003 | Doenges |
| 6,665,373 B1 | 12/2003 | Kotowski |
| 6,665,433 B2 | 12/2003 | Roder |
| 6,702,459 B2 | 3/2004 | Barnes |
| 6,763,635 B1 | 7/2004 | Lowman |
| 6,785,357 B2 | 8/2004 | Bernardi |
| 6,798,863 B2 | 9/2004 | Sato |
| 6,812,426 B1 | 11/2004 | Kotowski |
| 6,816,571 B2 | 11/2004 | Bijjani |
| 6,837,422 B1 | 1/2005 | Meder |
| 6,839,403 B1 | 1/2005 | Kotowski |
| 6,843,599 B2 | 1/2005 | Le |
| 6,876,719 B2 | 4/2005 | Ozaki |
| 6,879,657 B2 | 4/2005 | Hoffman |
| 6,920,197 B2 | 7/2005 | Kang |
| 6,922,460 B2 | 7/2005 | Skatter |
| 6,928,141 B2 | 8/2005 | Carver |
| 7,039,159 B2 | 5/2006 | Muenchau |
| 7,092,485 B2 | 8/2006 | Kravis |
| 7,099,434 B2 | 8/2006 | Adams |
| 7,103,137 B2 | 9/2006 | Seppi |

(56) References Cited

U.S. PATENT DOCUMENTS

| | | | |
|---|---|---|---|
| RE39,396 E | 11/2006 | Swift | |
| 7,162,005 B2 | 1/2007 | Bjorkholm | |
| 7,203,276 B2 | 4/2007 | Arsenault | |
| 7,207,713 B2 | 4/2007 | Lowman | |
| 7,218,704 B1 | 5/2007 | Adams | |
| 7,322,745 B2 | 1/2008 | Agrawal | |
| 7,333,587 B2 | 2/2008 | De Man | |
| 7,369,463 B1 | 5/2008 | Van Dullemen | |
| 7,369,643 B2 | 5/2008 | Kotowski | |
| 7,379,530 B2 | 5/2008 | Hoff | |
| 7,400,701 B1 | 7/2008 | Cason | |
| 7,486,768 B2 | 2/2009 | Allman | |
| 7,505,556 B2 | 3/2009 | Chalmers | |
| 7,517,149 B2 | 4/2009 | Agrawal | |
| 7,519,148 B2 | 4/2009 | Kotowski | |
| 7,551,715 B2 | 6/2009 | Rothschild | |
| 7,555,099 B2 | 6/2009 | Rothschild | |
| 7,593,506 B2 | 9/2009 | Cason | |
| 7,720,195 B2 | 5/2010 | Allman | |
| 7,742,568 B2 | 6/2010 | Smith | |
| 7,783,004 B2 | 8/2010 | Kotowski | |
| 7,809,109 B2 | 10/2010 | Mastronardi | |
| 7,817,776 B2 | 10/2010 | Agrawal | |
| 7,876,880 B2 | 1/2011 | Kotowski | |
| 7,963,695 B2 | 6/2011 | Kotowski | |
| 7,995,705 B2 | 8/2011 | Allman | |
| 8,000,436 B2 | 8/2011 | Seppi | |
| 8,059,781 B2 | 11/2011 | Agrawal | |
| 8,073,099 B2 | 12/2011 | Niu | |
| 8,194,822 B2 | 6/2012 | Rothschild | |
| 8,275,091 B2 | 9/2012 | Morton | |
| 8,503,605 B2* | 8/2013 | Morton et al. | 378/57 |
| 8,804,899 B2* | 8/2014 | Morton | 378/9 |
| 2004/0141584 A1 | 7/2004 | Bernardi | |
| 2005/0180542 A1 | 8/2005 | Leue | |
| 2007/0009088 A1 | 1/2007 | Edic | |
| 2008/0037707 A1 | 2/2008 | Rothschild | |
| 2009/0067575 A1 | 3/2009 | Seppi | |
| 2009/0086907 A1 | 4/2009 | Smith | |
| 2009/0116617 A1 | 5/2009 | Mastronardi | |
| 2011/0019799 A1 | 1/2011 | Shedlock | |
| 2011/0064192 A1 | 3/2011 | Morton | |
| 2011/0127426 A1* | 6/2011 | Akery | 250/306 |
| 2011/0206179 A1* | 8/2011 | Bendahan | 378/19 |
| 2011/0228896 A1* | 9/2011 | Peschmann | 378/5 |
| 2012/0273684 A1* | 11/2012 | Akery | 250/360.1 |

FOREIGN PATENT DOCUMENTS

| | | |
|---|---|---|
| EP | 1135700 | 3/2005 |
| EP | 1254384 | 1/2008 |
| EP | 2054741 | 5/2009 |
| EP | 1733213 | 2/2010 |
| EP | 2049888 | 5/2014 |
| GB | 2277013 A | 10/1994 |
| WO | 9802763 A1 | 1/1998 |
| WO | 9803889 A1 | 1/1998 |
| WO | 9820366 A1 | 5/1998 |
| WO | 9939189 A2 | 8/1999 |
| WO | 2004010127 A1 | 1/2004 |
| WO | 2009027667 A2 | 3/2009 |
| WO | 2013116549 | 8/2013 |

OTHER PUBLICATIONS

Chou, C, "Fourier coded-aperture imaging in nuclear medicine", IEEE Proc. Sci. Meas. Technol., vol. 141. No. 3, May 1994, pp. 179-184.

European Patent Office Summons to attend oral proceedings pursuant to Rule 115{1} EPC, Application No. 05743513.3-2204/1733213, dated May 6, 2009, 3 pages.

European Patent Office, International Search Report and Written Opinion of the International Searching Authority, PCT/US2005/011382, Oct. 21, 2005.

European Patent Office, International Search Report, International Application No. PCT/US99/28266, dated Sep. 6, 2000, 3 pages.

International Search Report, PCT/US2007/066936; dated: Sep. 30, 2008, 5 pages.

European Patent Office, International Search Report, PCT/US1998/18642, dated Jul. 7, 1999, 6 pages.

International Search Report, PCT/US1999/028035, dated Sep. 15, 2000, 6 pages.

Written Opinion of the International Searching Authority, PCT/US2007/066936, dated Sep. 30, 2008, 7 pages.

International Bureau of WIPO, International Preliminary Report on Patentability, PCT/US2005/011382, dated Oct. 19, 2006, 7 pages.

Mertz, L.N., et al, "Rotational aperture synthesis for x rays", Journal. Optical Society of America, vol. 3, Dec. 1986, pp. 2167-2170.

International Search Report for PCT/US13/24191, Rapiscan Systems Inc., mailed on Jun. 25, 2013.

* cited by examiner

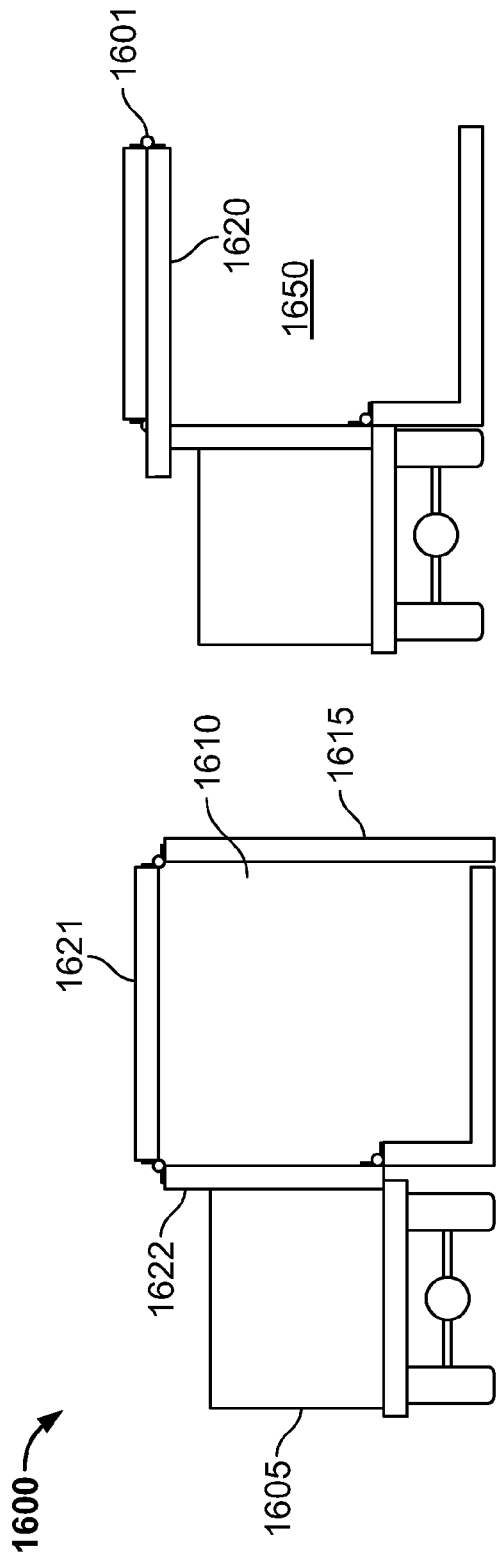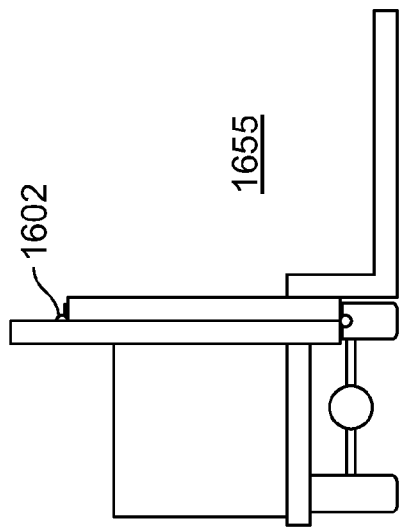

COMBINED SCATTER AND TRANSMISSION MULTI-VIEW IMAGING SYSTEM

CROSS-REFERENCE

The present application relies on U.S. Patent Provisional Application No. 61/594,625, filed on Feb. 3, 2012 for priority. The aforementioned application is herein incorporated by reference.

FIELD OF THE INVENTION

The present specification relates generally to the field of X-ray imaging system for security scanning and more specifically to multi-view X-ray scanning systems that advantageously combine transmission and backscatter imaging.

BACKGROUND

With the proliferation of terrorism and contraband trade, there exists an imminent need for systems that can effectively and efficiently screen cars, buses, larger vehicles and cargo to detect suspicious threats and illegal substances.

In the past, many technologies have been assessed for use in security inspection, and often X-ray imaging has been identified as a reasonable technique for such purposes. Several known X-ray scanning systems have been deployed for screening cars, buses and other vehicles. Such systems include transmission and backscatter X-ray screening systems. These prior art X-ray systems provide scanning from a very limited number of orientations, typically one and potentially two. For example, a transmission X-ray system may be configured in a side-shooter or top-shooter configuration. Backscatter systems may be available in single sided or, occasionally, in a three sided configuration.

Accordingly, there is need in the prior art for a multi-view imaging system which can have an arbitrary number of views, and typically more than one. There is also need in the art for a modular multi-view system that results in high detection performance at very low dose using a combination of backscatter and transmission imaging methodologies.

SUMMARY OF THE INVENTION

The present specification discloses, in one embodiment, an X-ray inspection system comprising an X-ray source configured to emit an X-ray beam; and a detector array comprising a plurality of non-pixellated detectors, wherein at least a portion of said non-pixellated detectors are not oriented toward the X-ray source.

In another embodiment, the present specification discloses an X-ray inspection system comprising at least two X-ray sources, wherein each X-ray source is configured to emit an X-ray beam; and at least two detector arrays, wherein each detector array comprises a plurality of non-pixellated detectors, wherein at least a portion of said non-pixellated detectors are oriented toward both X-ray sources.

In yet another embodiment, the present specification discloses a multi-view X-ray inspection system having a three-view configuration comprising three X-ray sources, wherein each X-ray source rotates and is configured to emit a rotating X-ray pencil beam; and at least two detector arrays, wherein each detector array comprises a plurality of non-pixellated detectors, wherein at least a portion of said non-pixellated detectors are oriented toward both X-ray sources.

In an embodiment, the X-ray beam is a pencil beam and each X-ray source rotates over an angle of rotation, and the X-ray inspection system has an intrinsic spatial resolution and wherein said intrinsic spatial resolution is determined by a degree of collimation of the X-ray beam and not by a degree of pixellation of X-ray scan data. Further, in an embodiment, a single detector is exposed to only one X-ray beam from one of said X-ray sources at a specific point in time, and each detector defines a plane and wherein said plane is offset from each plane defined by each X-ray source. In an embodiment, each detector has a rectangular shape.

In another embodiment of the present invention, the X-ray inspection system comprises at least one X-ray source configured to emit an X-ray beam; and a detector array comprising at least two rectangular profile backscatter detectors and a square profile transmission detector positioned between said at least two rectangular profile backscatter detectors.

In yet another embodiment, the present specification discloses an X-ray inspection system comprising at least one X-ray source configured to emit an X-ray beam; and a detector array comprising at least two rectangular profile backscatter detectors, a square profile transmission detector positioned between said at least two rectangular profile backscatter detectors, and a pair of fixed collimators positioned between the square profile transmission detector and one of said at least two rectangular profile backscatter detectors.

In an embodiment, an X-ray inspection system comprising a control system wherein, when said X-ray inspection system is activated to detect gamma rays, said control system turns off an X-ray source and switches a detector data processing mode from current integrating mode to a pulse counting mode, is disclosed.

In another embodiment, the present invention discloses an X-ray inspection system having at least one X-ray source, wherein said X-ray source comprises an extended anode X-ray tube, a rotating collimator assembly, a bearing, a drive motor, and a rotary encoder.

In yet another embodiment, the present invention discloses, an X-ray inspection system having at least one X-ray source, wherein said X-ray source comprises an extended anode X-ray tube, a rotating collimator assembly, a bearing, a drive motor, a secondary collimator set, and a rotary encoder.

In an embodiment, an X-ray inspection system comprising a control system wherein said control system receives speed data and wherein said control system adjusts at least one of a collimator rotation speed of an X-ray source, data acquisition rate, or X-ray tube current based upon said speed data, is disclosed.

In another embodiment, the present specification discloses an X-ray inspection system comprising a control system wherein said control system adjusts at least one of a collimator rotation speed of an X-ray source, data acquisition rate, or X-ray tube current to ensure a uniform dose per unit length of an object being scanned.

The present specification is also directed toward an X-ray inspection system for scanning an object, the inspection system comprising: at least two rotating X-ray sources configured to simultaneously emit rotating X-ray beams, each of said X-ray beams defining a transmission path; at least two detector arrays, wherein each of said at least two detector arrays is placed opposite one of the at least two X-ray sources to form a scanning area; and at least one controller for controlling each of the X-ray sources to scan the object in a coordinated manner, such that the X-ray beams of the at least two X-ray sources do not cross transmission paths.

In one embodiment, each of the emitted X-ray beams is a pencil beam and each X-ray source rotates over a predetermined angle of rotation.

In one embodiment, each detector is a non-pixellated detector.

In one embodiment, a first, a second and a third rotating X-ray sources are configured to simultaneously emit rotating X-ray beams, wherein the first X-ray source scans the object by starting at a substantially vertical position and moving in a clockwise manner; wherein the second X-ray source scans the object by starting at a substantially downward vertical position and moving in a clockwise manner; and wherein the third X-ray source scans the object by starting at a substantially horizontal position and moving in a clockwise manner.

In one embodiment, the controller causes each X-ray source to begin scanning the object in a direction that does not overlap with an initial scanning direction of any of the remaining X-ray sources, thereby eliminating cross talk among the X-ray sources.

In one embodiment, a plurality of scanned views of the object are collected simultaneously with each detector being irradiated by no more than one X-ray beam at any one time.

In one embodiment, a volume of the detectors is independent of a number of scanned views of the object obtained.

In one embodiment, the X-ray inspection system has an intrinsic spatial resolution wherein said intrinsic spatial resolution is determined by a degree of collimation of an X-ray beam.

In one embodiment, the one or more detectors comprise an array of scintillator detectors having one or more photomultiplier tubes emerging from an edge of the detector array to allow X-ray beams from adjacent X-ray sources to pass an unobstructed face of the detector array opposite to the photomultiplier tubes.

In one embodiment, the one or more detectors are formed from a bar of a scintillation material that has a high light output efficiency, a fast response time and is mechanically stable over large volumes with little response to changing environmental conditions.

In one embodiment, the one or more detectors are gas ionization detectors comprising a Xenon or any other pressurized gas.

In one embodiment, the one or more detectors are formed from a semiconductor material such as but not limited to CdZnTe, CdTe, HgI, Si and Ge.

In one embodiment, the X-ray inspection system is configured to detect gamma rays by turning off the X-ray sources switching the detectors from a current integrating mode to a pulse counting mode.

The present specification is also directed toward an X-ray inspection system for scanning an object, the inspection system comprising: at least two X-ray sources configured to simultaneously emit rotating X-ray beams for irradiating the object, wherein each of said X-ray beams defines a transmission path; a detector array comprising at least one transmission detector placed between at least two backscatter detectors, wherein each of said backscatter detectors detects backscattered X-rays emitted by a first X-ray source placed on a first side of the object and wherein the transmission detectors detects transmitted X-rays emitted by a second X-ray source placed on an opposing side of the object; and at least one controller for controlling each of the X-ray sources to concurrently scan the object in a coordinated, non-overlapping, manner such that the transmission paths of each of said X-ray beams does not cross.

In one embodiment, the detector array comprises at least two rectangular profile backscatter detectors and a square profile transmission detector positioned between said at least two rectangular profile backscatter detectors.

In another embodiment, the detector array comprises a transmission detector positioned between two backscatter detectors wherein the detectors are placed within a single plane facing the object begin scanned and the transmission detector has a smaller exposed surface area than each of the backscatter detectors.

In one embodiment, the X-ray inspection system further comprises a pair of fixed collimators positioned between the transmission detector and one of said at least two backscatter detectors.

In one embodiment, each of the X-ray sources comprises an extended anode X-ray tube, a rotating collimator assembly, a bearing, a drive motor, and a rotary encoder.

In another embodiment, each of the X-ray sources comprises: an extended anode X-ray tube coupled with a cooling circuit, the anode being at ground potential; a rotating collimator assembly comprising at least one collimating ring with slots cut at predefined angles around a circumference of the collimator, a length of each slot being greater than a width and an axis of rotation of the slot, and the width of the slots defining an intrinsic spatial resolution of the X-ray inspection system in a direction of the scanning; a bearing for supporting a weight of the collimator assembly and transferring a drive shaft from the collimator assembly to a drive motor; a rotary encoder for determining an absolute angle of rotation of the X-ray beams; and a secondary collimator set for improving spatial resolution in a perpendicular scanning direction.

In one embodiment, the controller receives speed data comprising a speed of the object and, based upon said speed data, adjusts at least one of a collimator rotation speed of an X-ray source, a data acquisition rate, or an X-ray tube current based upon said speed data.

The aforementioned and other embodiments of the present shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings:

FIG. 16a shows a mobile inspection system in its operating state ready for scanning;

FIG. 16b shows the step of folding up of vertical boom about a hinge point at the end of horizontal boom;

FIG. 16c shows the step of folding up the horizontal boom and, concurrently, the vertical boom around a hinge point at the top of a vertical support;

DETAILED DESCRIPTION OF THE INVENTION

The present specification is directed towards an X-ray scanning system that advantageously combines image information from both backscatter and transmission technologies. More specifically, the present invention employs four discrete backscatter systems, however re-uses the pencil beam from one backscatter system to illuminate large area detectors from a second backscatter system so that simultaneous multi-sided backscatter and transmission imaging using the same set of four X-ray beams can be achieved. This approach is cost effective, in that it saves the cost of a segmented detector array yet still provides a comprehensive inspection.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
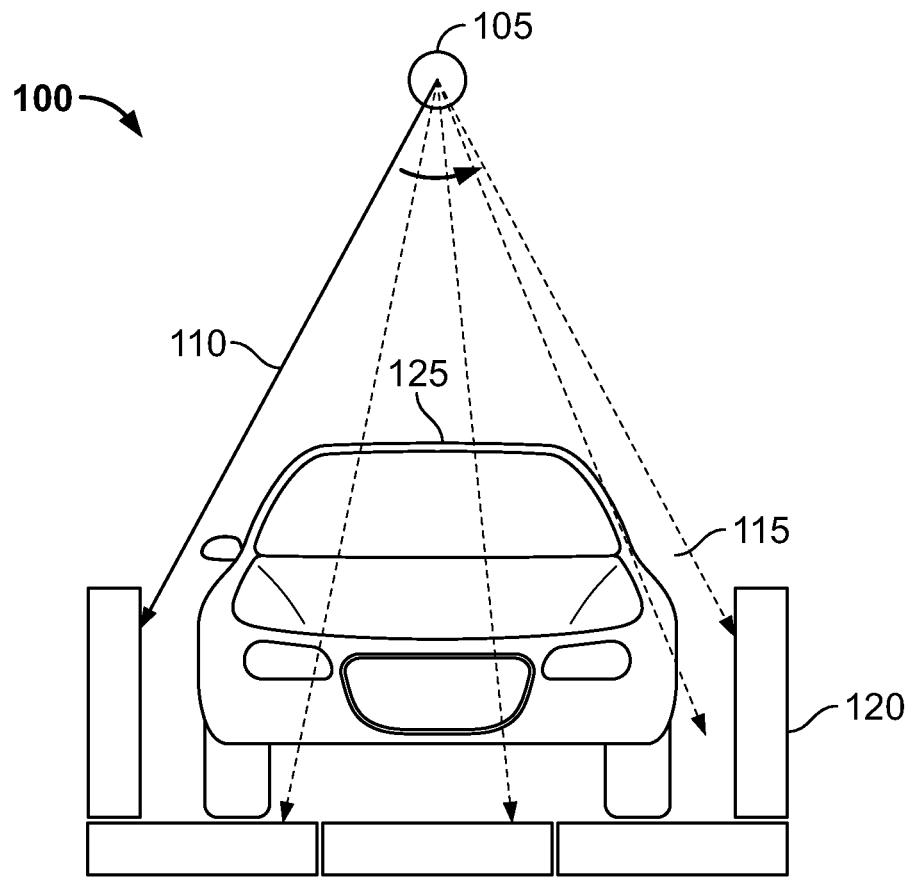
FIG. 1 shows a single-view top-shooter transmission imaging system in accordance with one embodiment of the present invention.

FIG. 1 shows a single-view top-shooter transmission imaging system 100 in accordance with an embodiment of the present invention. System 100 comprises an X-ray source 105 with a rotating pencil beam collimator. When the X-ray beam is on, the collimator rotates continuously to form a moving X-ray beam 110 that sweeps over a fan-shaped area 115. A series of X-ray detectors 120 are placed in a transmission inspection geometry, namely opposite the X-ray beam 110 and with the inspected object between the detectors 120 and X-ray beam 110, to record the intensity of the X-ray beam 110 once it has passed through object 125, such as a vehicle. In one embodiment, detectors 120 are on the order of 1000 mm long and stacked end-to-end to form a linear sensor having a length equal to a plurality of meters. An advantage of such detectors is that they can be fabricated quite inexpensively, since they do not have spatial resolution.

An X-ray scan image, of the object 125, is formed by recording intensity of signal at output of each detector 120 at all times, as well as the angle of rotation of the X-ray pencil beam 110. In radial coordinates, object X-ray transmission is determined by plotting the recorded X-ray intensity from X-ray detectors 120 which is being pointed to by the X-ray beam 110 against its angle of rotation at any given instant. As known to persons of ordinary skill in the art a predetermined coordinate transform maps this data back onto a Cartesian grid or any other chosen co-ordinate grid.

In contrast to typical prior art X-ray imaging systems, the intrinsic spatial resolution of the system 100 is determined not by pixellation of the X-ray scan data but by collimation of the X-ray beam 110 at the source 105. Since the X-ray beam 110 is produced from a small focal spot with finite area, the X-ray pencil beam 110 is diverging and therefore the spatial resolution of the system 100 varies with distance of the detectors 120 from the source 105. Therefore, spatial resolution of the system 100 is least in the lower corners directly opposite to the X-ray source 105. However, this varying spatial resolution is corrected by deconvolution of the spatial impulse response of the system 100 as a function of rotation angle to thereby produce an image with constant perceptible spatial resolution.

Figure 2:
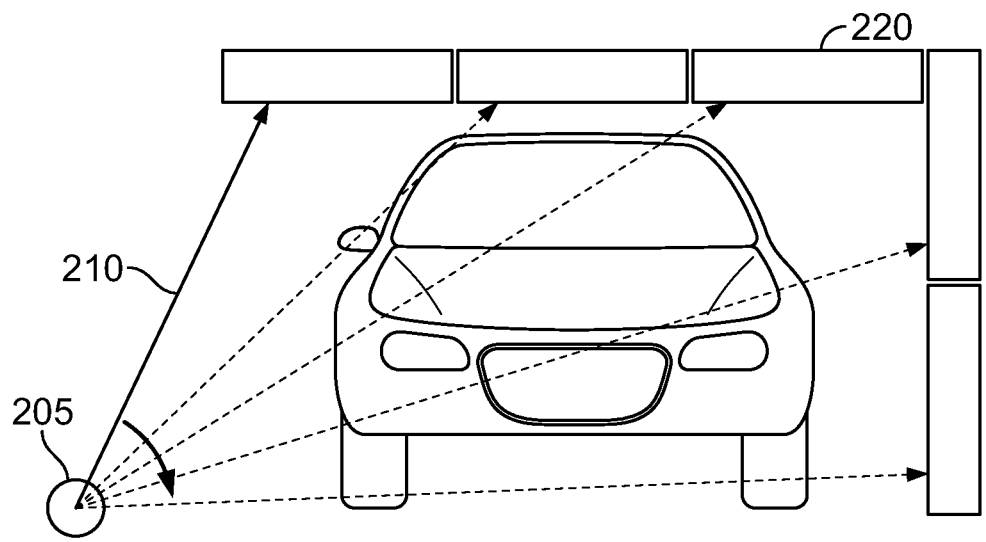
FIG. 2 is a first side-shooter configuration of one embodiment of the present invention.
Figure 3:
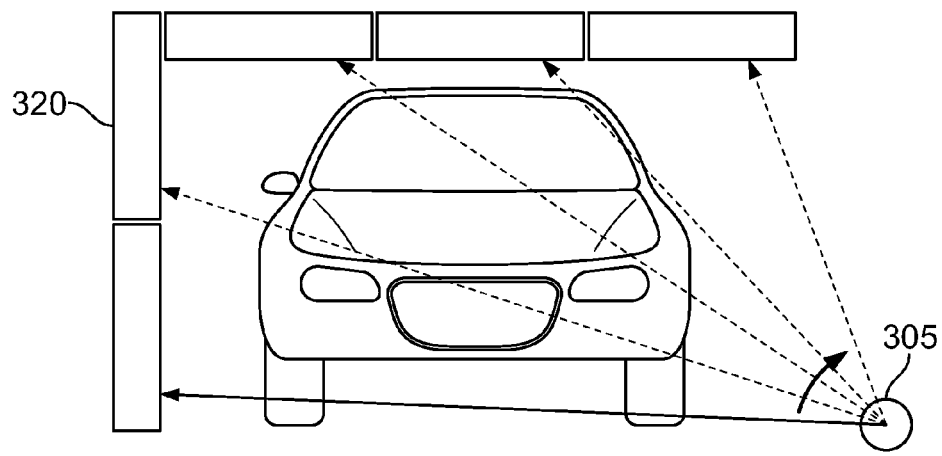
FIG. 3 is a second side-shooter configuration of one embodiment of the present invention.

FIG. 2 is a side-shooter configuration, of the system 100 of FIG. 1, that uses a similar identical X-ray source 205 with a rotating pencil beam 210 and a series of identical X-ray detectors 220 but in alternative locations. As shown in FIG. 3, a mirrored side-shooter configuration is achieved using the same X-ray source 305 and detectors 320 but in a mirror image configuration to that shown in FIG. 2.

Figure 4:
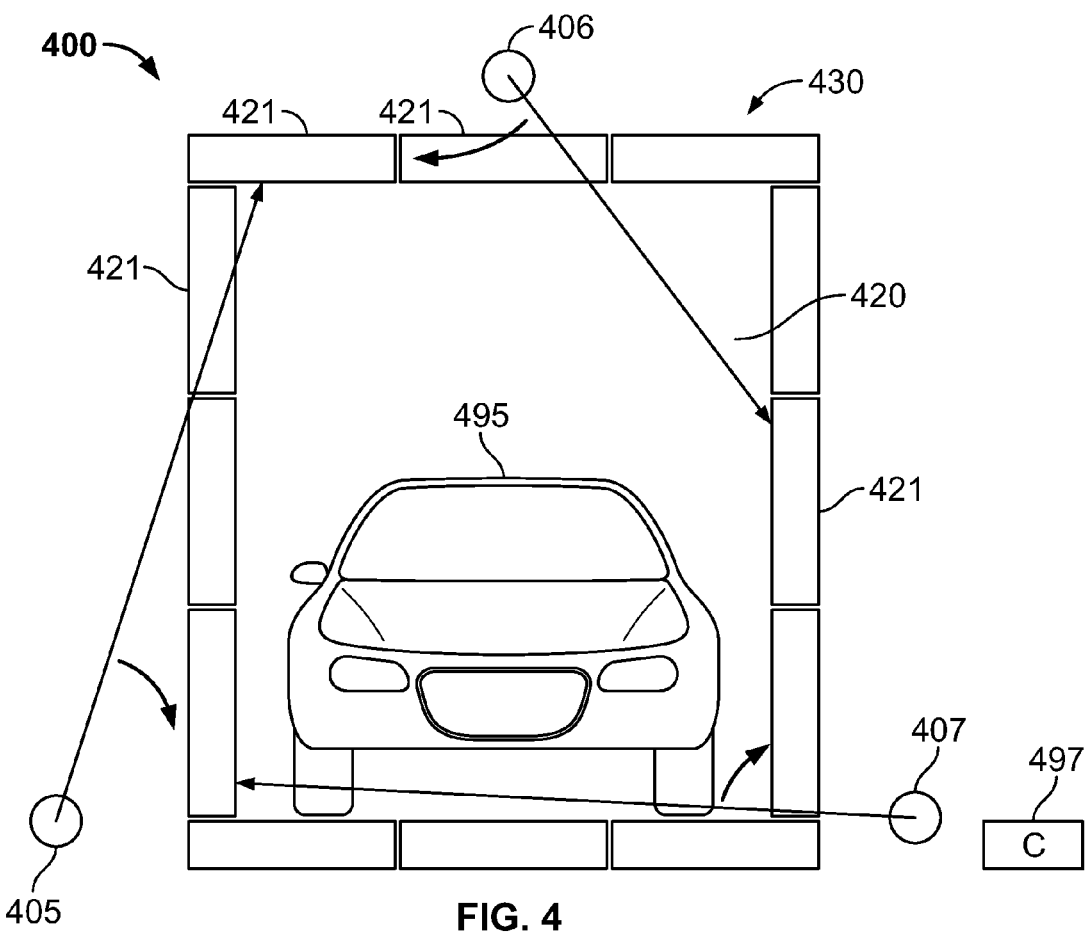
FIG. 4 is a multi-view X-ray imaging system embodiment of the present invention.

FIG. 4 is a multi-view X-ray imaging system 400 that integrates the configurations of FIGS. 1 through 3 in accordance with an embodiment of the present invention. In one embodiment, system 400 has a three-view configuration enabled by three simultaneously active rotating X-ray beams 405, 406 and 407 with plurality of detectors placed correspondingly, in one embodiment, in transmission configuration to form a scanning tunnel 420. System 400 provides a high degree of inspection capability, in accordance with an object of the present invention, while at the same time achieving this at substantially low X-ray dose since the volume of space irradiated at any moment in time is low compared to conventional prior art line scan systems that typically have large numbers of pixellated X-ray detectors and fan-beam X-ray irradiation.

As shown in FIG. 4, there is almost no cross talk between the three X-ray views which are collected simultaneously because the X-ray sources 405, 406, 407, are controlled by at least one controller 497, which may be local to or remote from the X-ray sources 405, 406, 407, that transmits control signals to each X-ray source 405, 406, 407 in a manner that causes them to scan the target object 495 in a coordinated, and non-overlapping, manner. In one embodiment, X-ray source 405 scans object 495 by starting at a substantially vertical position (between 12 o'clock and 1 o'clock) and moving in a clockwise manner. Concurrently, X-ray source 406 scans object 495 by starting at a substantially downward vertical position (around 4 o'clock) and moving in a clockwise manner. Concurrently, X-ray source 407 scans object 495 by starting at a substantially horizontal position (around 9 o'clock) and moving in a clockwise manner. It should be appreciated that each of the aforementioned X-ray sources could begin at a different position, provided that a) each starts a scan in a direction that does not overlap with the initial scanning direction of the other X-ray sources and b) each scans in a direction and at a speed that does not substantially overlap with the scan of the other X-ray sources.

According to an aspect of the present invention, there is almost no limit to the number of views which may be collected simultaneously in the system 400 with each detector segment 421 being irradiated by no more than one primary X-ray beam at any one time. In one embodiment, the detector configuration 430, shown in FIG. 4, comprises 12 detector segments 421 each of approximately 1 m in length to form an inspection tunnel of approximately 3 m (Width)×3 m (Height). In one embodiment, the detector configuration 430 is capable of supporting six independent X-ray views to allow transition of the sweeping X-ray views between adjacent detectors. An alternate embodiment comprising 0.5 m long detector segments 421 is capable of supporting up to 12 independent X-ray image views.

Persons of ordinary skill in the art should appreciate that, in system 400, the volume of detector material is independent of the number of views to be collected and the density of readout electronics is quite low compared to conventional prior art pixellated X-ray detector arrays. Additionally, a plurality of X-ray sources can be driven from a suitably rated high voltage generator thereby enabling additional X-ray sources to be added relatively simply and conveniently. These features enable the high density multi-view system 400 of the present invention to be advantageously used in security screening applications.

Figure 5:
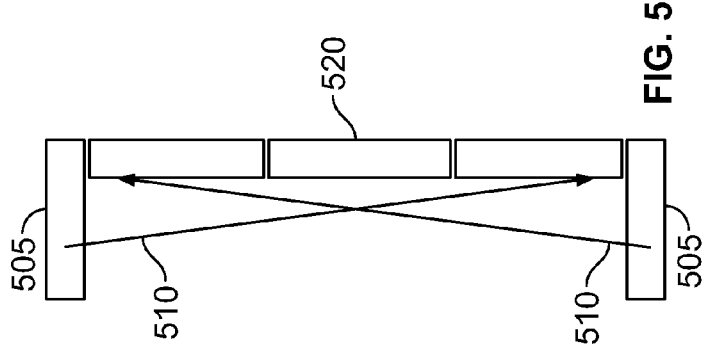
FIG. 5 shows X-ray detector offset geometry from a plane of X-ray sources for use in the multi-view X-ray imaging system of the present invention.

As shown in FIG. 5, a multi-view system, such as that shown in FIG. 4, has X-ray detectors 520 offset from the plane of the X-ray sources 505. The offset prevents X-ray beams 510 from being absorbed relatively strongly in the detector nearest to it, before the beam can enter the object under inspection.

According to another aspect, X-ray detectors are not required to have a spatial resolving function thereby allowing the primary beam to wander over the face of the detector, and to a side face of the detector, with minimal impact on overall performance of the imaging system. This considerably simplifies the detector configuration in comparison to a conventional prior art pixellated X-ray system, since, in a pixellated system, each detector needs to be oriented to point back towards a corresponding source to maintain spatial resolution. Thus, in prior art pixellated X-ray systems, a single detector cannot point to more than one source position and, therefore, a dedicated pixellated array is needed for each source point.

Figure 6:
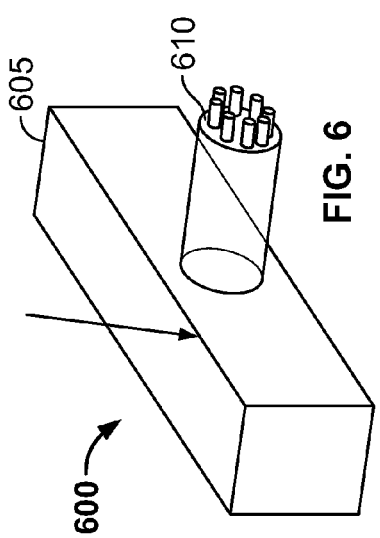
FIG. 6 shows an embodiment of a suitable X-ray detector for use in the multi-view system of the present invention.

FIG. 6 shows an embodiment of a suitable X-ray detector 600 for use in a multi-view system (such as the three-view system 400 of FIG. 4) of the present invention. As shown, detector 600 is formed from a bar 605 of X-ray detection material, that in one embodiment is fabricated from scintillation material. In a scintillation process, X-ray energy is converted to optical photons and these photons are collected using a suitable optical detector, such as a photomultiplier tube or photodiode 610. Suitable scintillation detection materials comprise plastic scintillators, CsI, BGO, NaI, or any other scintillation material known to persons of ordinary skill in the art that has high light output efficiency, fast time response and is mechanically stable over large volumes with little response to changing environmental conditions. Alternatively, detector materials can also comprise gas ionisation and gas proportional detectors, ideally with pressurised gas to enhance detection efficiency and high electric field strengths for improving signal collection times. Noble gas based detectors such as pressurised Xenon detectors are quite suitable for use with the multi-view system of present invention. Semiconductor detector materials could also be adopted, such as CdZnTe, CdTe, HgI, Si and Ge, although the capacitance, response time, costs and temperature response of these materials make them a less preferred choice.

Figure 7B:
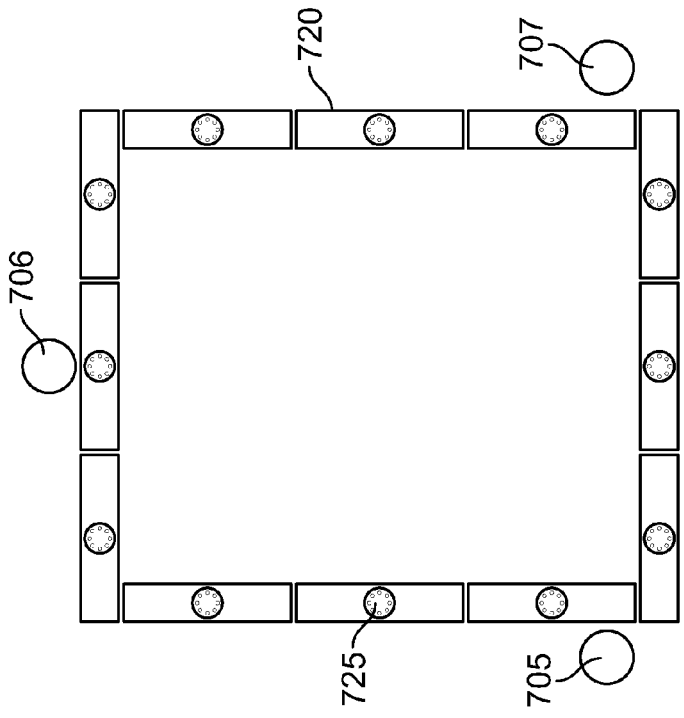
FIG. 7b is an end view of the detector array for use in the multi-view system of the present invention.
Figure 7A:
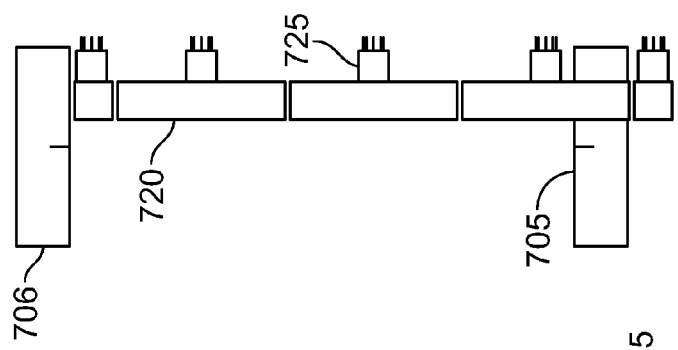
FIG. 7a is a side view of a detector array for use in the multi-view system of the present invention.

An array of scintillator detectors 720 is shown in FIGS. 7a and 7b with photomultiplier tubes 725 emerging from the same long edge of scintillating material to allow X-ray beams from adjacent X-ray sources to pass the unobstructed face of the detector opposite to the photomultiplier tubes 725. Two X-ray sources 705, 706 are visible in the side view of the detector array 720 of FIG. 7a. Three X-ray sources 705, 706, 707 are visible in the end view of FIG. 7b.

From X-rays which are transmitted straight through an object and to a set of transmission detectors on the opposite side of the object, a fraction of the X-rays scatter from the object into other directions. It is known to those of ordinary skill in the art that the probability of detecting a scattered X-ray varies with the inverse square of distance of the detector from the scattering site. This means that a detector placed proximate to an X-ray beam, as it enters the object, will receive a much larger backscatter signal than a detector placed at significant distance from X-ray source.

Figure 8:
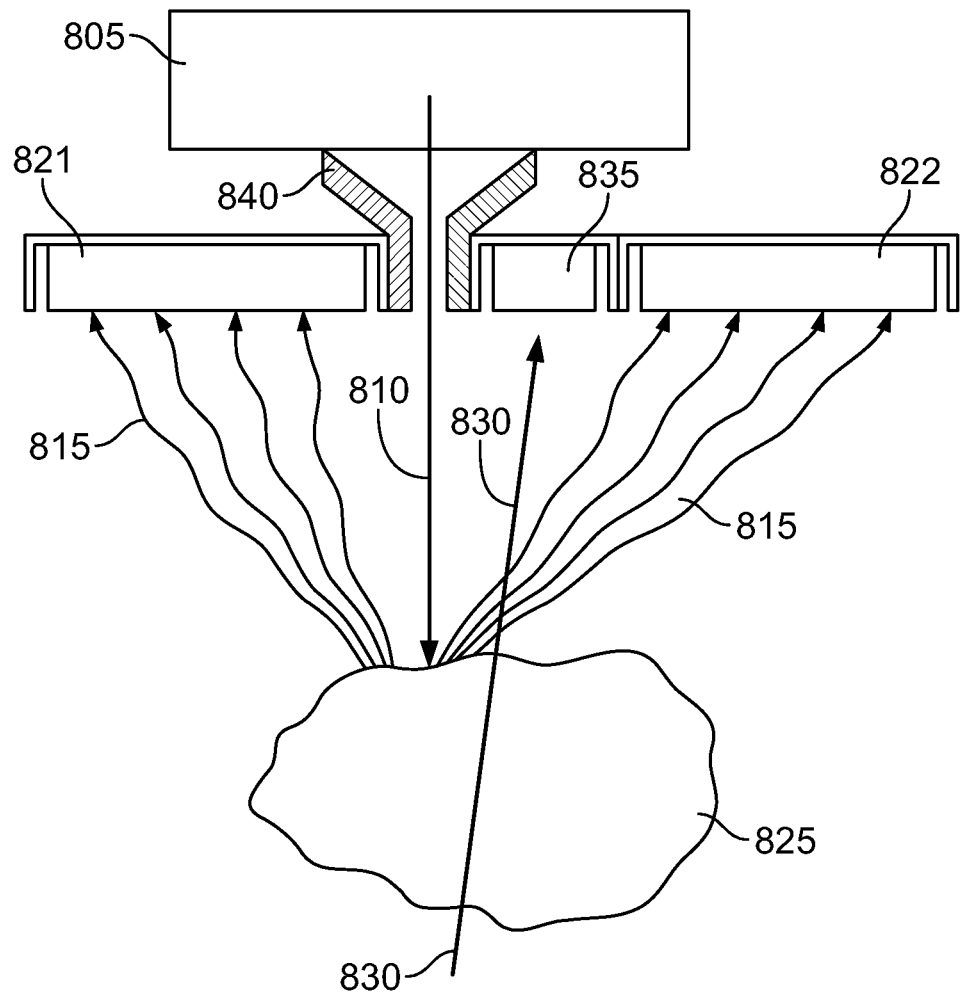
FIG. 8 shows an embodiment of a backscatter-transmission detector configuration for use with multi-view system of the present invention.

FIG. 8 shows an embodiment of a detector configuration for use with multi-view system of the present invention to utilize X-rays backscattered from an object under inspection, in addition to transmitted X-rays. In this embodiment, an X-ray source 805 illuminates object 825 with a scanning pencil beam 810 of X-rays. A fraction of the X-rays 815 backscatter, which are then sensed by a pair of rectangular detectors 821, 822. Transmission X-ray beam 830 from a second X-ray source (not shown) at the other side of the object 825, is captured at a smaller square section detector 835.

It should be noted herein that the detectors can be of any shape and are not limited to a rectangular shape. In this particular embodiment, a rectangular shape is selected because it produces a uniform response and has a relatively manufacturing cost. In addition, a rectangular shape is easier to stack end-to-end compared with a circular or other curved detector. Similarly, using a smaller square cross-section will most likely yield the most uniform response, for example, when compared to a cylindrical detector with a circular cross section, and is relatively lower in cost to manufacture.

The square profile transmission detector 835 is placed between the two rectangular profile backscatter detectors 821, 822. A pair of fixed collimators 840 substantially reduces the effect of scattered radiation on the transmission detector 835, resulting from a nearby X-ray source, which measures relatively weak transmission signals from the opposing X-ray source (not shown). All detectors 821, 822 and 835 are shielded using suitable materials, such as steel and lead, around all faces except their active faces to avoid background signal due to natural gamma-radiation and unwanted X-ray scattering. Therefore, a transmission detector is sandwiched between two backscatter detectors, within a single plane facing the object begin scanned, and the transmission detector has a smaller exposed surface area than each of the backscatter detectors.

Figure 9:
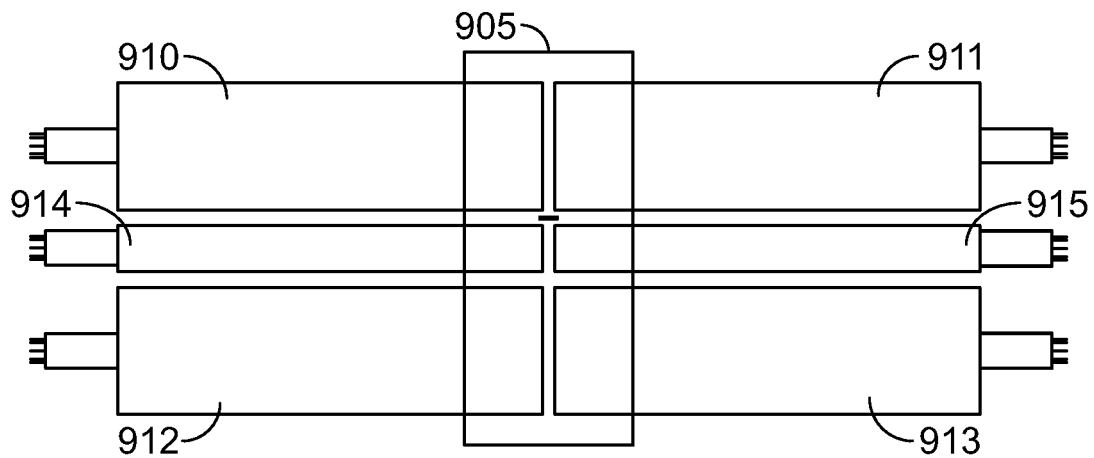
FIG. 9 shows an alternate embodiment of the backscatter-transmission detector configuration for use with multi-view system of the present invention.

FIG. 9 shows an alternate embodiment of combined X-ray backscatter-transmission detectors. Here, a large imaging panel 900, which in one embodiment ranges from 1.5 m to 3.0 m in total length, comprises six individual X-ray detectors in addition to a scanning X-ray source 905. Four of the detectors 910, 911, 912 and 913 are used for recording X-ray backscatter from the local X-ray source 905, while two detectors 914, 915 having smaller exposed surface areas than each of the backscatter detectors 910, 911, 912, 913 are used to record transmission X-ray signals from an opposing X-ray generator.

Persons of ordinary skill in the art should note that with the detector configurations of FIGS. 8 and 9, a multi-view backscatter system of the present invention is achieved that has one backscatter view corresponding to each transmission view.

According to a further aspect, transmission imaging detectors can also be used for recording backscatter signals when not being directly irradiated by a transmission imaging beam. However, use of additional detection sensors, as shown in FIGS. 8 and 9 substantially improve sensitivity of the backscatter detectors albeit at substantially higher cost. Therefore, a low cost system with modest backscatter performance can be assembled using just a single detector array in offset geometry as shown in FIGS. 5 and 6.

In one embodiment, the additional backscatter imaging panels are formed from a low cost high volume detector material such as scintillation materials comprising plastic scintillators, scintillation screens such as $GdO_2S$ with optical light guides, and solid scintillators such as CsI and NaI although any scintillator known to those of ordinary skill in the art may be used, providing it has a fast response time (<10 us primary decay time), good uniformity, and stability against change in ambient conditions. Semiconductor and gas filled detectors may also be used, although these are less preferred with the exception of pressured Xenon gas detectors.

According to yet another aspect of the present invention, the large area array of detector panels of FIGS. 8 and 9 are also used as passive detectors of gamma radiation such as that emitted from special nuclear materials and other radioactive sources of interest such as Co-60, Cs-137 and Am-241. To enable system sensitivity to passive gamma rays, the X-ray sources are turned off and the detector electronics switched from a current integrating mode to a pulse counting mode. The object, such as a vehicle, under inspection is first scanned with the X-ray system of the present invention. It should be noted herein that the method of the present invention can be used in a single-view configuration or a multi-view configuration. If a suspicious item is detected, the vehicle is re-scanned, this time, in passive detection mode. This provides dual operating function capability for the imaging system of the present invention. Further, due to spatial positioning of the detector panels, it is possible to approximately localize radioactive source in space (recognizing the inverse square reduction of count rate at detectors due to the distance of the detector from the source). This localization is applied to the multi-view X-ray images in the form of a graphic overlay to show the position of a passive gamma source.

Figure 10:
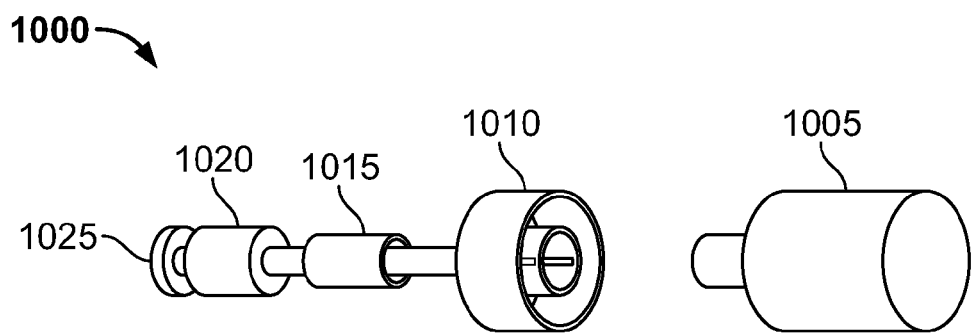
FIG. 10 shows an embodiment of a suitable scanning X-ray source for use with multi-view system of the present invention.

As shown in FIG. 10, an embodiment of a suitable scanning X-ray source 1000, for use with multi-view system of the present invention, comprises an extended anode X-ray tube 1005, a rotating collimator assembly 1010, a bearing 1015, a drive motor 1020, and a rotary encoder 1025.

In one embodiment, extended anode X-ray tube 1005 has the anode at ground potential. The anode is provided with a cooling circuit to minimize the thermal heating of the target during extended operating periods. In one embodiment, a rotating collimator assembly 1010 is advantageously formed from suitable engineering materials such as steel and tungsten. The collimator comprises at least one collimating ring with slots cut at appropriate angles around circumference of the collimator. The length of each slot is greater than its width and is longer than its axis of rotation and narrow in the direction of rotation. Width of the slots defines intrinsic spatial resolution of the transmission imaging system in the direction of the scanning.

Bearing 1015 supports the weight of the collimator assembly 1010 and transfers a drive shaft from the collimator assembly to a drive motor 1020. The drive motor 1020 is capable of being speed controlled using an electronic servo drive to maintain exact speed of rotation. A rotary encoder 1025 provides absolute angle of rotation since this is required to determine the position of each sampled detector point in the final generated image.

Figure 11A:
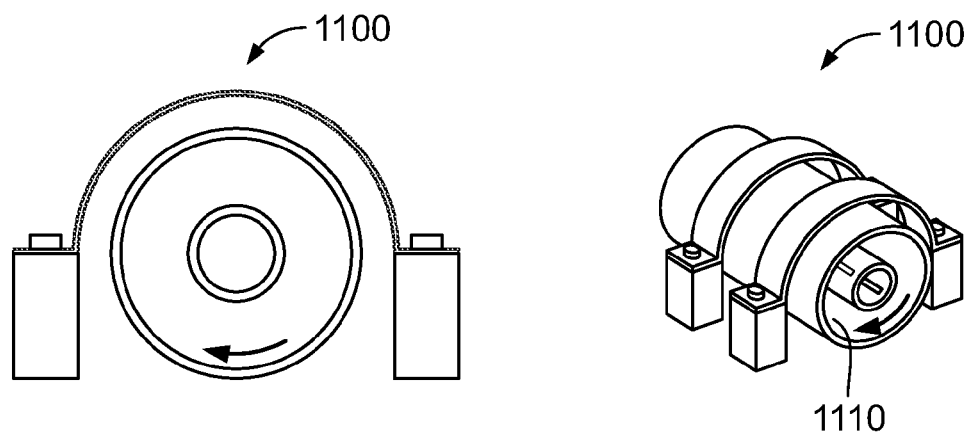
FIG. 11a shows a secondary collimator set to improve spatial resolution in the perpendicular direction.
Figure 11B:
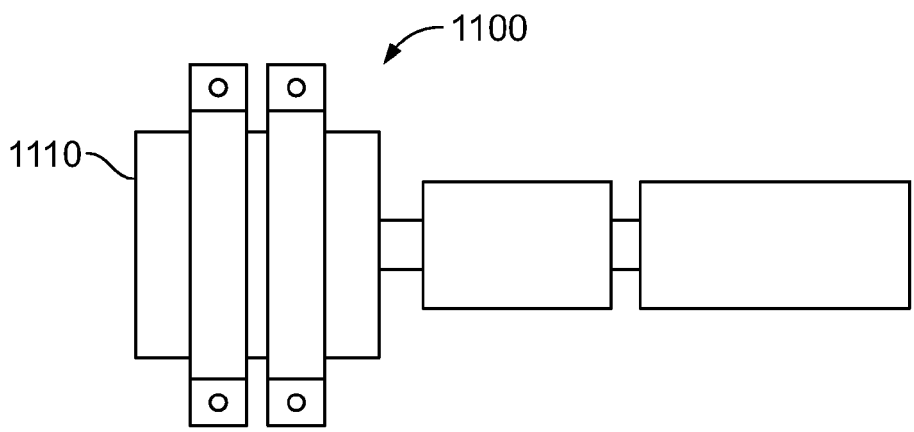
FIG. 11b shows the secondary collimator set of FIG. 11a positioned around an outer edge of a rotating collimator.

The rotating X-ray beam produced by the source 1000 of FIG. 10 has good resolution in one dimension only. To improve spatial resolution in the perpendicular direction, a secondary collimator set is provided as shown in FIGS. 11a and 11b. Referring now to FIGS. 11a and 11b simultaneously, hoop-like collimators 1100 are placed around outer edge of the rotating collimator 1110 to provide collimation into beam width direction. Since in one embodiment transmission detectors are likely to be of a square section (such as detectors 835 of FIG. 8) and. when combined with offset system geometry of the present invention (as discussed with reference to FIG. 5), use of a secondary beam width collimator 1110 allows a specific shape of beam to be produced which precisely follows the center line of the imaging detectors.

In an embodiment of the present invention, additional collimation is placed at transmission detectors to constrain the width of X-ray beam before it enters the detection material itself. This allows an image of arbitrary spatial resolution to be collected even if an actual X-ray beam passing through object is of lower intrinsic spatial resolution. The width of the X-ray beam passing through the object is kept as small as possible, but consistent with the final collimator slot width, in order to minimise dose to the object under inspection.

Figure 12:
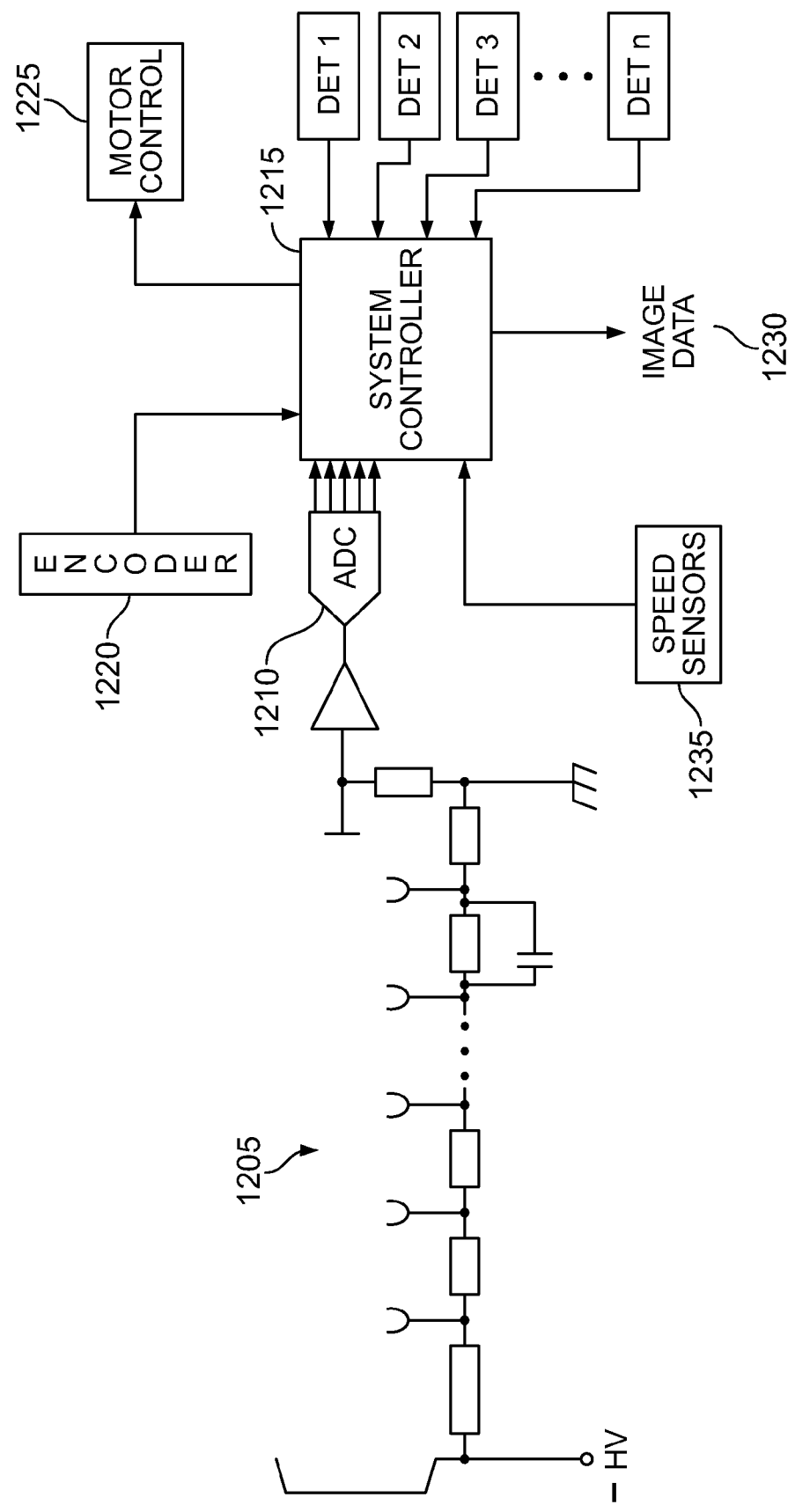
FIG. 12 shows an embodiment of read-out electronic circuit for use with detectors of the multi-view system of the present invention.

Each detector in the multi-view system is provided with readout electronics which biases the photodetector, buffers and amplifies output signal from the photodetector and digitizes the resulting signal. FIG. 12 shows an embodiment of photomultiplier tube circuit 1205 with buffer amplifier and high speed analogue-to-digital (ADC) converter 1210. Data from the ADC 1210 is transferred into a system controller circuit 1215 along with digital data from all of the other photodetectors ($DET_1$, $DET_2$, ..., $DET_n$). The system controller 1215 also takes in encoder data 1220 from each of X-ray sources and provides motor drive signals 1225 to each X-ray source. Thus, the system controller 1215 coordinates data acquisition between each component of the detector system and generates an image data stream 1230 which provides data individually for each transmission and backscatter X-ray view.

A set of suitable sensors 1235 are used to measure speed of the vehicle or object under inspection as it passes through the inspection region. Suitable sensors comprise microwave radar cameras, scanning infra-red lasers or simply inductive sensors placed at known distance apart which can provide a measurement of speed (=distance/time) by comparing the times at which each sensor goes from false to true and vice versa as the vehicle scans past. This speed information, in one embodiment, is passed to the system controller 1215 which then adjusts collimator rotation speed, data acquisition rate and X-ray tube current to ensure a uniform dose per unit length of the object being scanned. By using a high speed ADC 1210, multiple samples are acquired at each transmission and backscatter source point so that an average value, or otherwise filtered value, is stored to improve signal-to-noise ratio of the imaging system.

The linear scanning velocity of X-ray beams across the face of a transmission imaging detector varies as a function of the distance from the source (i.e., more distant points suffer a faster linear scan rate). Therefore, in one embodiment, use of a high speed oversampling analogue-to-digital converter 1210 simplifies the adjustment of sample time to match the linear scanning velocity using, for example, encoder data 1220 to trigger the start of each sampling period, where the relevant encoder values are stored in a digital lookup table prior to the start of scanning. Sampling of data at a high speed allows for an improved deconvolution of the spatial resolution in the scanning direction by oversampling the measured data and generating a lower sample rate output image data compared to that which would be achieved by trying to deconvolve only a low sample rate image.

According to an embodiment, the system controller 1215 is advantageously designed using a combination of digital electronics, such as a field programmable gate array, and a microcontroller. The digital circuits provide precise timing that is required to build up a scanned image from multiple detectors and multiple encoders in an automated fashion, using only data from the encoders 1220 to coordinate activity. One or more microcontrollers provide system configuration capability, in-system programmability for field upgrade of firmware, and support for final data transmission process.

Figure 13:
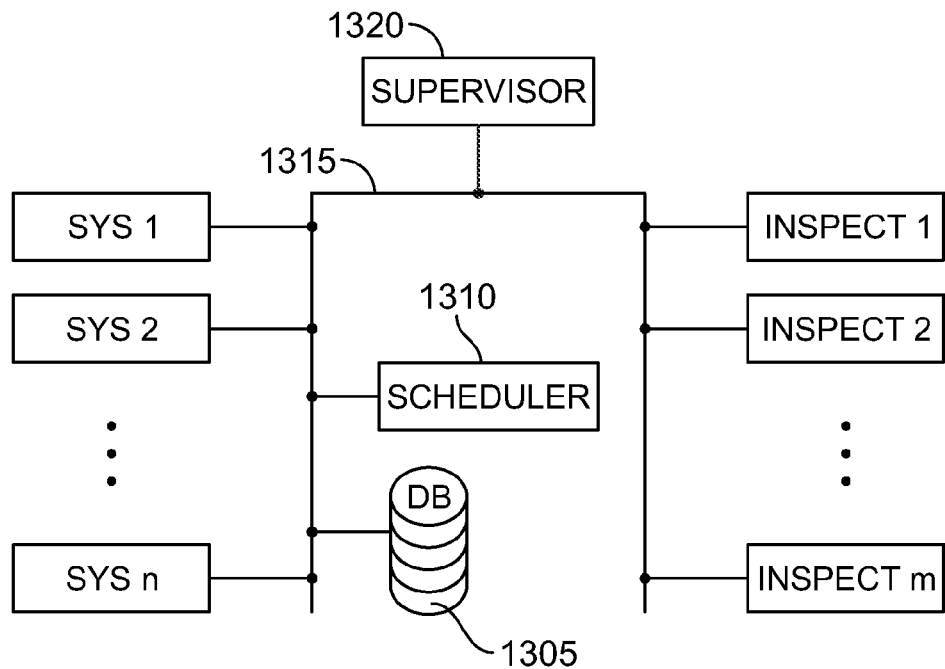
FIG. 13 shows a matrixed configuration where a set of 'n' multi-view imaging systems are monitored by a group of 'm' image inspectors.

An embodiment utilizes a matrixed configuration where a set of 'n' multi-view imaging systems are monitored by a group of 'm' image inspectors. In this configuration, as shown in FIG. 13, each imaging system $SYS_1$, $SYS_2$, ... $SYS_n$ is connected to a network 1315 which provides a database 1305 for storage and recall of all image data. A job scheduler 1310 keeps track of which systems are online and of which operators $INSPECT_1$, $INSPECT_2$, ... $INSPECT_m$ are available for inspection. Images from the database 1305 are transferred automatically to the next available inspector for review. Inspection results are passed back to the relevant imaging system which advantageously comprises traffic control measures to direct manual search of suspect vehicles or objects under inspection. System supervisor 1320 is, in one embodiment, a manager who can monitor the state of the imaging systems, monitor the efficiency of the operators and can double-check inspection results from inspectors.

Figure 14:
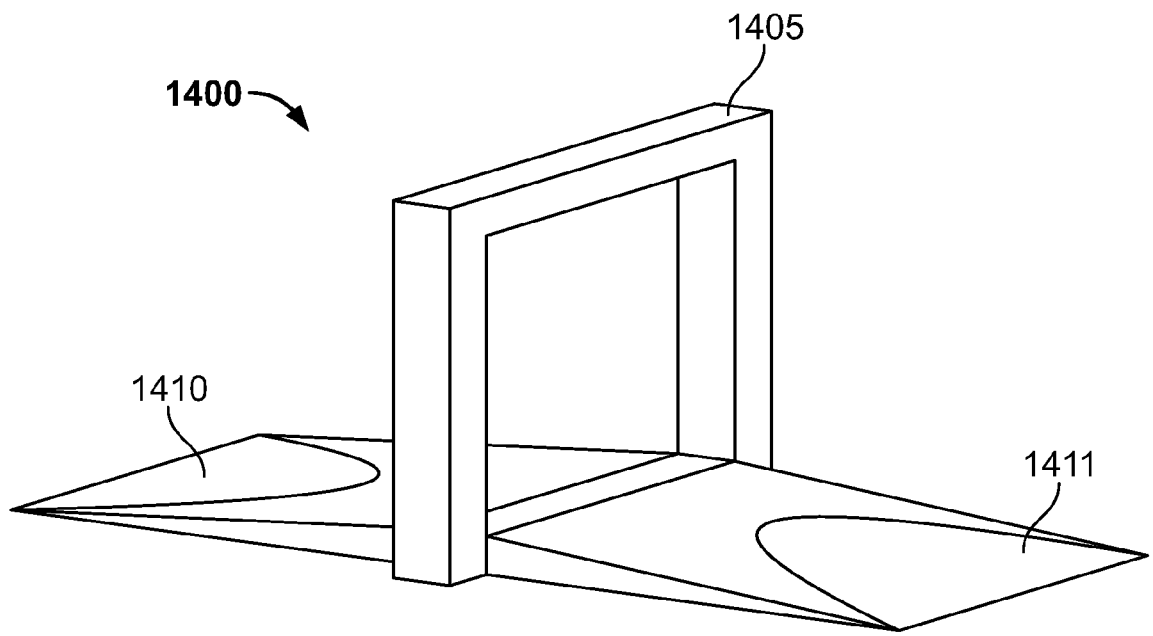
FIG. 14 shows a deployment of a multi-view imaging system to scan cargo, in accordance with an embodiment of the present invention.

FIG. 14 shows deployment of multi-view imaging system to scan cargo, in accordance with an embodiment of the present invention, comprising a gantry 1400 with main imaging system (such as the three-view system 400 of FIG. 4) at its center along with drive-up and drive-down ramps 1410, 1411 respectively provided to allow vehicles to pass through the centre of the inspection tunnel 1405. In an alternate embodiment, the gantry 1400 is provided with a conveyor to transport cargo through the inspection tunnel 1405. In one embodiment, suitable tunnel sizes are up to 800 mm×500 mm for small baggage, up to 1800 mm×1800 mm for packets and small cargo, up to 3000 mm×3000 mm for small vehicles and large cargo and up to 5500 mm×4000 mm for large vehicles and containerized cargo.

Figure 15:
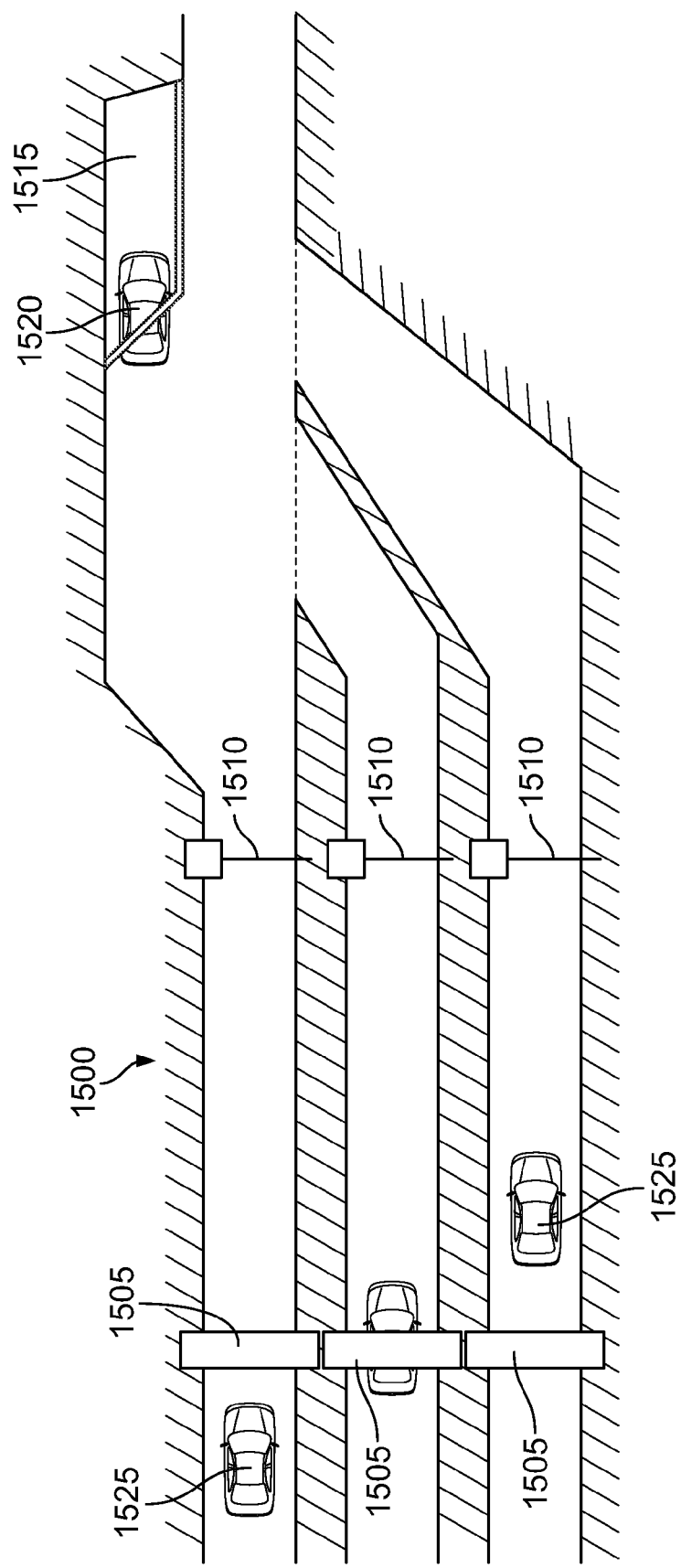
FIG. 15 shows a deployment of a multi-view imaging system to scan occupied vehicles in accordance with an embodiment of the present invention.

FIG. 15 shows deployment of multi-view imaging system to scan occupied vehicles in accordance with an embodiment of the present invention, where vehicles in a multi-lane road 1500 approach a plurality of scanners 1505, one scanner per lane. Vehicles 1525 are scanned as they pass through respective scanners and approach a plurality of corresponding traffic control systems 1510 such as barrier or other suitable traffic control measures, including traffic lights. Decision results from image inspectors are passed automatically to these traffic control systems 1510 which then hold or divert traffic as necessary. In an example illustration, a holding area 1515 is shown with a vehicle 1520 parked therein as a result of an inspector/operator marking scanned image of the vehicle 1520 as suspicious.

In accordance with another aspect, the multi-view imaging system of the present invention is deployed in the form of a mobile inspection vehicle for rapid relocation to an inspection site. FIG. 16a shows mobile inspection system 1600 in its operating state ready for scanning. Vehicle 1605 carries an embodiment of a multi-view detection system, where a scanning tunnel 1610 is surrounded by a set of booms 1615, 1621, 1622.

An exemplary boom stow sequence is graphically illustrated using FIGS. 16b through 16g as follows:

FIG. 16b shows step 1650 comprising the folding up of vertical boom 1620 about a hinge point 1601 at the end of horizontal boom 1621. This can be achieved, for example, by using a hydraulic cylinder actuation although other mechanisms known to those of ordinary skill in the art may be considered such as pull wires and electronic drivers.

Step 1655, shown in FIG. 16c, comprises the simultaneous folding up of horizontal boom 1621 and vertical boom 1620 about a hinge point 1602 which is positioned at the top of vertical support boom 1622.

Figure 16D:
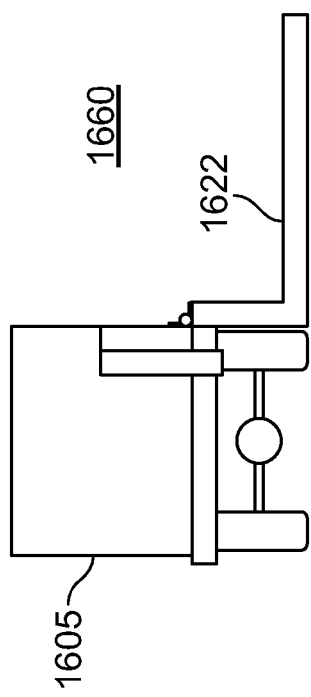
FIG. 16d shows the step of laying down the vertical boom toward the back of the mobile inspection vehicle.

Step 1660, shown in FIG. 16d, comprises lowering vertical support boom 1622 toward the back of the vehicle 1605. Vertical support boom 1622 may be folded down to a steep angle to allow room for an operator inspection cabin to be co-located on the back of the vehicle. In another embodiment, vertical support boom 1622 may be folded down to be substantially parallel to the back platform of the vehicle to allow a compact system configuration which is advantageously developed to allow rapid re-location of systems using conventional air transportation.

Figure 16E:
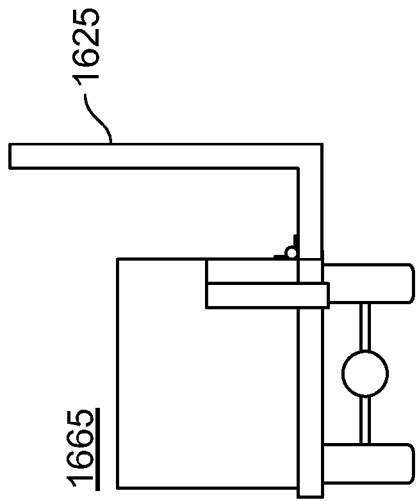
FIG. 16e shows the step of folding up the bottom imaging section by at least 90 degrees from its operating position.
Figure 16F:
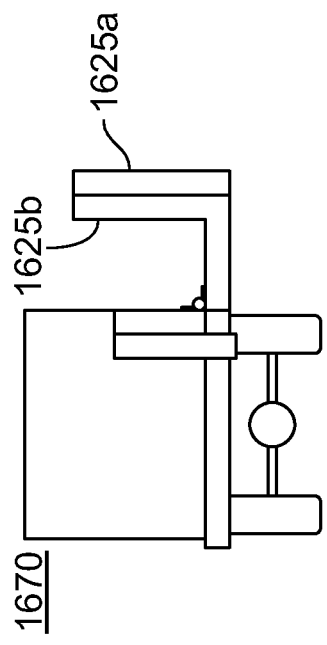
FIG. 16f shows the step of folding an outer horizontal base section by 180 degrees to cause it to lie parallel to inner base section.

Step 1665, shown in FIG. 16e, comprises folding up the base section 1625 of the imaging system by at least 90 degrees from its operating position. Thereafter, in step 1670, as shown in FIG. 16f, comprises folding the outer horizontal base section 1625a of the main base section 1625 by 180 degrees so that it lies parallel to the inner base section 1625b.

Figure 16G:
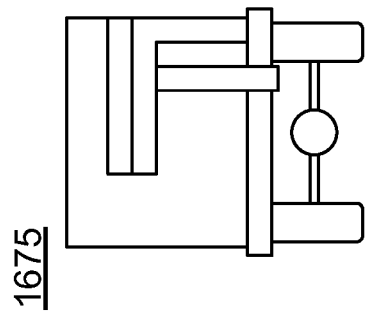
FIG. 16g shows the step of completely folding the base section by 90 degrees to complete the system stow.

Finally, in step 1675, shown in FIG. 16g a complete folding of the base section occurs by a 90 degree rotation to complete system stow. The aforementioned steps, 1650 through 1675, for boom deployment to obtain operating state of FIG. 16a comprise boom stow steps in reverse sequence.

In alternate embodiments, the mobile inspection system 1600 is deployed with only the vertical and horizontal booms and not the lower imaging section. This gives dual view imaging capability in side-shooter configuration but no top-shooter view. In this mode, the system is capable of full drive-by scanning mode with an imaging configuration of at least one transmission view, with or without backscatter capability.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. An X-ray inspection system for scanning an object, the inspection system comprising:
   a first X-ray source and a second X-ray source, each configured to simultaneously emit rotating X-ray beams for irradiating the object, wherein each of said X-ray beams defines a transmission path;
   a detector array comprising at least one transmission detector placed between at least two backscatter detectors, wherein each of said backscatter detectors detects backscattered X-rays emitted by the first X-ray source placed on a first side of the object and wherein the transmission detectors detects transmitted X-rays emitted by the second X-ray source placed on an opposing side of the object; and
   at least one controller for controlling each of the first and second X-ray sources to concurrently scan the object in a coordinated, non-overlapping, manner such that the transmission paths of each of said X-ray beams does not cross.

2. The X-ray inspection system as claimed in claim 1 wherein the detector array comprises at least two rectangular profile backscatter detectors and a square profile transmission detector positioned between said at least two rectangular profile backscatter detectors.

3. The X-ray inspection system as claimed in claim 1 wherein the detector array comprises a transmission detector positioned between two backscatter detectors and wherein the detectors are placed within a single plane facing the object begin scanned and the transmission detector has a smaller exposed surface area than each of the backscatter detectors.

4. The X-ray inspection system as claimed in claim 1 further comprising a pair of fixed collimators positioned between the transmission detector and one of said at least two backscatter detectors.

5. The X-ray inspection system as claimed in claim 1 wherein each of the X-ray sources comprises an extended anode X-ray tube, a rotating collimator assembly, a bearing, a drive motor, and a rotary encoder.

6. The X-ray inspection system as claimed in claim 1 wherein each of the first and second X-ray sources comprises:
   an extended anode X-ray tube coupled with a cooling circuit, the anode being at ground potential;
   a rotating collimator assembly comprising at least one collimating ring with slots cut at predefined angles around a circumference of the collimator, a length of each slot being greater than a width and an axis of rotation of the slot, and the width of the slots defining an intrinsic spatial resolution of the X-ray inspection system in a direction of the scanning;
   a bearing for supporting a weight of the collimator assembly and transferring a drive shaft from the collimator assembly to a drive motor;
   a rotary encoder for determining an absolute angle of rotation of the X-ray beams; and
   a secondary collimator set for improving spatial resolution in a perpendicular scanning direction.

7. The X-ray inspection system as claimed in claim 6 wherein the controller receives speed data comprising a speed of the object and, based upon said speed data, adjusts at least one of a collimator rotation speed of an X-ray source, a data acquisition rate, or an X-ray tube current based upon said speed data.

* * * * *